(12) United States Patent
Miyamoto et al.

(10) Patent No.: US 9,097,718 B2
(45) Date of Patent: Aug. 4, 2015

(54) METHOD AND DEVICE FOR DETECTING NUCLEIC ACID, AND KIT

(75) Inventors: Shigehiko Miyamoto, Hyogo (JP); Takaaki Jikihara, Hyogo (JP); Sotaro Sano, Hyogo (JP); Koji Takahashi, Hyogo (JP); Jun Tomono, Hyogo (JP)

(73) Assignee: Kaneka Corporation, Osaka (JP)

( * ) Notice: Subject to any disclaimer, the term of this patent is extended or adjusted under 35 U.S.C. 154(b) by 110 days.

(21) Appl. No.: 13/823,946

(22) PCT Filed: Sep. 21, 2011

(86) PCT No.: PCT/JP2011/071477
§ 371 (c)(1),
(2), (4) Date: Jun. 11, 2013

(87) PCT Pub. No.: WO2012/039422
PCT Pub. Date: Mar. 29, 2012

(65) Prior Publication Data
US 2013/0252341 A1     Sep. 26, 2013

(30) Foreign Application Priority Data
Sep. 22, 2010   (JP) ................................ 2010-211889

(51) Int. Cl.
*G01N 33/58* (2006.01)
*G01N 21/78* (2006.01)
*C12Q 1/68* (2006.01)

(52) U.S. Cl.
CPC .............. *G01N 33/583* (2013.01); *C12Q 1/686* (2013.01); *C12Q 1/6816* (2013.01); *C12Q 1/6846* (2013.01); *G01N 21/78* (2013.01); *Y10T 436/143333* (2015.01)

(58) Field of Classification Search
CPC .. C12Q 2563/173; C12Q 1/68; C12Q 1/6816; C12Q 1/6846; C12Q 1/686; G01N 21/78; G01N 33/583; Y10Y 436/43333
USPC ............. 436/63, 94, 106, 109, 110, 111, 119, 436/120, 124, 127, 131, 164, 165, 166, 177, 436/178; 422/400, 413, 420, 430, 68.1, 422/82.05, 82.09, 534, 551; 435/6.1, 6.12
See application file for complete search history.

(56) References Cited

U.S. PATENT DOCUMENTS 5,049,490 A * 9/1991 Sutherland et al. .......... 435/6.18
6,645,758 B1 11/2003 Schnipelsky et al.
(Continued)

FOREIGN PATENT DOCUMENTS

CN      1826171 A    8/2006
CN    102356161 A    2/2012
(Continued)

OTHER PUBLICATIONS

Gibson et al., "A Colorimetric Assay for Phosphate to Measure Amplicon Accumulation in Polymerase Chain Reaction", Analytical Biochemistry, vol. 254, No. 245, 1997, pp. 18-22, XP055099501.
Yang et al., "Counterion-dye staining method for DNA in agarose gels using crystal violet and methyl orange", Electrophoresis, vol. 22, 2001, pp. 855-859, XP055099507.
Cong et al., "A visible dye-based staining method for DNA in polyacrylamide gels by ethyl violet", Analytical Biochemistry, vol. 402, No. 1, 2010, pp. 99-101, XP055099508.
(Continued)

*Primary Examiner* — Maureen Wallenhorst
(74) *Attorney, Agent, or Firm* — Novak Druce Connolly Bove + Quigg LLP (57) ABSTRACT

The present invention provides a method for detecting a nucleic acid, by which a multi-stranded nucleic acid amplified by a nucleic acid amplification method is detected easily and with a high degree of accuracy without the need for specialized equipment, and also provides a nucleic acid detection device. Provided are a method for detecting a nucleic acid under visible light via a color reaction produced by contact between a chromogenic leuco dye and the multi-stranded nucleic acid, as well as a nucleic acid detection device using this method.

19 Claims, 2 Drawing Sheets

(56) References Cited

U.S. PATENT DOCUMENTS

| | | | |
|---|---|---|---|
| 2004/0171016 A1 | 9/2004 | Tomita et al. | |
| 2005/0019944 A1* | 1/2005 | Qiao et al. | 436/169 |
| 2005/0112770 A1* | 5/2005 | Nakamura et al. | 436/94 |
| 2010/0330564 A1* | 12/2010 | Tomono | 435/6 |
| 2011/0117549 A1* | 5/2011 | Miyamoto et al. | 435/6 |

FOREIGN PATENT DOCUMENTS

| | | |
|---|---|---|
| EP | 0511712 A1 | 11/1992 |
| EP | 2410063 A1 | 1/2012 |
| JP | 5-237000 A | 9/1993 |
| JP | 9187275 A | 7/1997 |
| JP | 2003240780 A | 8/2003 |
| WO | WO-02/103053 A1 | 12/2002 |
| WO | WO-2005/016515 A2 | 2/2005 |
| WO | WO-2010/106977 A1 | 9/2010 |

OTHER PUBLICATIONS

Kong et al., "Fluorescent Sensor for Monitoring Structural Changes of G-Quadruplexes and Detection of Potassium Ion", Analytical Chemistry, vol. 81, No. 7, 2009, pp. 2678-2684, XP055099510.

Jin et al., "Usefulness of visible dyes for the staining of protein or DNA in electrophoresis", Electrophoresis, vol. 25, No. 15, 2004, pp. 2429-2438, XP055099512.

Miyamoto et al., "Pipette Tip-gata PCR Zofuku Hantei Tool D-Quick no Kaihatsu to sono Tokucho", JETI, 16 Sep. 2010, vol. 58, No. 10, pp. 60-63.

Partial translation of Funakoshi News, Feb. 1, 2011 Issue, p. 9.

Molecular Cloning Second Edition, vol. 1, 6.15, 1989, Gel Electrophoresis of DNA.

International Preliminary Report on Patentability issued in corresponding Application No. PCT/JP2011/071477 dated Apr. 16, 2013.

* cited by examiner

FIG.1

Developing direction

Amplified nucleic acid solution

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Primer F

<400> SEQUENCE: 1
ggaaacagct atgaccatga                                               20

<210> SEQ ID NO 2
<211> LENGTH: 19
<212> TYPE: DNA
<213> ORGANISM: Artificial Sequence
<220> FEATURE:
<223> OTHER INFORMATION: Primer F

<400> SEQUENCE: 2
ctatgcggca tcagagcag                                                19
```

METHOD AND DEVICE FOR DETECTING NUCLEIC ACID, AND KIT

CROSS REFERENCE TO RELATED APPLICATIONS

This application is a National Phase filing under 35 U.S.C. §371 of PCT/JP2011/071477 filed on Sep. 21, 2011; and this application claims priority to Application No. 2010-211889 filed in Japan on Sep. 22, 2010 under 35 U.S.C. §119; the entire contents of all are hereby incorporated by reference.

TECHNICAL FIELD

The present invention belongs to the technical field of methods for detecting multi-stranded nucleic acids, and devices or kits for detecting multi-stranded nucleic acids.

BACKGROUND ART

Methods for specifically amplifying target nucleic acids have become very important techniques in molecular biological research and in clinical applications including genetic testing.

The most widely used nucleic acid amplification method is the PCR (polymerase chain reaction) method, but this requires complex temperature control. Therefore, the LAMP (loop-mediated isothermal amplification) method, the ICAN (isothermal and chimeric primer-initiated amplification of nucleic acids) method and other isothermal amplification methods have also been developed.

Nucleic acids amplified by the PCR, LAMP and ICAN methods and the like are double strands, and methods using fluorescent dyes are being actively studied as detection methods for them.

The most common method is a method of performing agarose electrophoresis on a solution after the amplification reaction, followed by binding to a fluorescent intercalator such as ethidium bromide or SYBR Green and then observing the specific fluorescence (Non Patent Literature 1). However, the method of detection using a fluorescent intercalator after electrophoresis requires an electrophoresis running time of about 30 minutes to an hour, as well as expensive equipment such as a UV irradiation device or fluorescence detection device for detecting the fluorescence.

If there is no possibility of other DNAs being present and only the presence or absence of the amplified product needs to be determined, the electrophoresis step can be omitted by adding beforehand the fluorescent intercalator to the reaction liquid before the PCR reaction, and then detecting the fluorescence after the amplification reaction (Patent Literature 1). However, the problem is that since fluorescent intercalators bind to primers and other single-stranded nucleic acids, the background signals are then amplified, thereby leading to reduced detection sensitivity. In this context, a method has been developed for reducing background signals by treating with a compound that reacts preferentially with a fluorescent intercalator bound to a single-stranded nucleic acid (Patent Literature 2), and fluorescent dyes have been developed having improved reaction specificity to double-stranded nucleic acids compared to single-stranded nucleic acids (Patent Literature 3), but in both cases fluorescent detection is still used.

Alternatively, a method has been developed for detection by fluorescence polarization by performing a nucleic acid amplification reaction using a fluorescent labeled primer (Patent Literature 4), but in general fluorescent primers are expensive, and the method is also disadvantageous, for example, in that it is complex because it requires an operation to separate out the fluorescent labeled primer not incorporated into the amplified product.

CITATION LIST

Patent Literature
  Patent Literature 1: JP H05-237000 A
  Patent Literature 2: WO 2002/103053
  Patent Literature 3: JP 2003-240780 A
  Patent Literature 4: JP H09-187275 A
Non Patent Literature
  Non Patent Literature 1: Molecular Cloning Second Edition, vol. 1, 6.15 (1989)

SUMMARY OF INVENTION

Technical Problem

It is an object of the present invention to provide a method for detecting a multi-stranded nucleic acid, by which a multi-stranded nucleic acid amplified by a nucleic acid amplification reaction is detected easily and rapidly under visible light without the need for complex operations and specialized equipment, as well as a multi-stranded nucleic acid detection device or kit.

Solution to Problem

The inventors have found as a result of exhaustive research aimed at resolving these problems that when a multi-stranded nucleic acid is brought into contact with a chromogenic leuco dye, a leaving group of the leuco dye is dissociated, forming a color that allows the nucleic acid to be detected under visible light. The inventors have also found that a multi-stranded nucleic acid detection device or kit can be prepared using this principle, thereby completing the present invention.

Specifically, the present invention relates to a method for detecting a multi-stranded nucleic acid, comprising a step of bringing a chromogenic leuco dye into contact with a multi-stranded nucleic acid, wherein a color formed by interaction between the leuco dye and the multi-stranded nucleic acid is detected under visible light.

Preferably, the leuco dye is a compound represented by General Formula (I):

wherein $R^1$, $R^2$ and $R^3$ each independently represent a substituted or unsubstituted aryl group, and L represents —$SO_3R^4$, —$NO_3$, —$NO_2$, —CN, —X, —$NHR^5$, —$N(COR^6)(COR^7)$, —$SR^8$, —$SSR^9$, —$OR^{10}$, —$NHSNH_2$, —OH or —H, with $R^4$ representing an alkali metal or a hydrogen atom; X representing a halogen atom;
and $R^5$, $R^6$, $R^7$, $R^8$, $R^9$ and $R^{10}$ each independently representing an alkyl group, aryl group, acyl group, alkenyl group or alkynyl group, wherein a leaving group of the leuco dye is dissociated by interaction between the leuco dye and the multi-stranded nucleic acid, and a color that can be detected under visible light is then formed by dissociation of the leaving group.

The compound represented by General Formula (I) is preferably a compound represented by General Formula (II):

(II)

wherein L is defined as above; $R^{11}$ and $R^{12}$ each independently represent a substituted or unsubstituted aryl group; and $R^{13}$, $R^{14}$, $R^{15}$, $R^{16}$ and $R^{17}$ each independently represent a halogen atom or a carboxyl group, sulfo group, nitro group, cyano group, amido group, amino group, alkyl group, aryl group, alkenyl group, alkynyl group, hydroxy group, alkoxy group, aryloxy group, alkylthio group, arylthio group, alkylamino group, arylamino group, acyl group, alkoxycarbonyl group, aryloxycarbonyl group, alkylsulfonyl group or arylsulfonyl group.

The leuco dye is preferably a reaction product of a triarylmethane dye and a nucleophile.

The triarylmethane dye is preferably one or more dyes selected from the group consisting of gentian violet, crystal violet, methyl green, malachite green, victoria blue and pararosaniline, and derivatives thereof.

The nucleophile is preferably one or more nucleophiles selected from the group consisting of sulfite ions, hydrogen sulfite ions, nitrate ions, nitrite ions, cyanide ions, halide ions, nitrogen nucleophiles, sulfur nucleophiles, alkali metal alkoxides, alkali metal hydroxides and hydride nucleophiles.

The present invention also relates to a device or kit for detecting a multi-stranded nucleic acid, comprising: (d) a carrier carrying a leuco dye, (e) a pathway for a test sample to pass through the carrier (d), and (f) a part for detecting under visible light a color formed by interaction between the test sample and the leuco dye to determine the presence of a multi-stranded nucleic acid.

Preferably, the leuco dye is a compound represented by General Formula (I):

(I)

wherein $R^1$, $R^2$ and $R^3$ each independently represent a substituted or unsubstituted aryl group, and L represents $-SO_3R^4$, $-NO_3$, $-NO_2$, $-CN$, $-X$, $-NHR^5$, $-N(COR^6)(COR^7)$, $-SR^8$, $-SSR^9$, $-OR^{10}$, $-NHSNH_2$, $-OH$ or $-H$, with $R^4$ representing an alkali metal or a hydrogen atom; X representing a halogen atom; and $R^5$, $R^6$, $R^7$, $R^8$, $R^9$ and $R^{10}$ each independently representing an alkyl group, aryl group, acyl group, alkenyl group or alkynyl group, wherein a leaving group of the leuco dye is dissociated by interaction between the leuco dye and the multi-stranded nucleic acid, and a color that can be detected under visible light is then formed by dissociation of the leaving group.

The carrier (d) preferably carries a liquid mixture of a triarylmethane dye and a nucleophile.

The triarylmethane dye is preferably one or more dyes selected from the group consisting of gentian violet, crystal violet, methyl green, malachite green, victoria blue and pararosaniline, and derivatives thereof.

The nucleophile is preferably one or more nucleophiles selected from the group consisting of sulfite ions, hydrogen sulfite ions, nitrate ions, nitrite ions, cyanide ions, halide ions, nitrogen nucleophiles, sulfur nucleophiles, alkali metal alkoxides, alkali metal hydroxides and hydride nucleophiles.

Advantageous Effects of Invention

With the method of the present invention, the presence or absence of nucleic acid synthesis or amplification can be detected visually via a color reaction produced by contact between a multi-stranded nucleic acid and a leuco dye, without the use of specialized detection equipment. Moreover, with the nucleic acid detection device of the present invention, a test substance can be rapidly detected visually via a color reaction by simply adding the test sample containing a multi-stranded nucleic acid to the device.

DESCRIPTION OF EMBODIMENTS

The present invention is described in detail below.
1. Method for Detecting Nucleic Acid The present invention relates to a method for detecting a multi-stranded nucleic acid, comprising a step of bringing a chromogenic leuco dye into contact with a multi-stranded nucleic acid, wherein a color formed by interaction between the leuco dye and the multi-stranded nucleic acid is detected under visible light.

Multi-stranded nucleic acids to be detected include double-stranded nucleic acids, triple-stranded nucleic acids and quadruple-stranded nucleic acids. Known as nucleic acids are DNA, RNA and many chemically modified forms of these, as well as nucleic acid analogs called PNAs having polypeptide chains as the backbone, and the like, and all these are included in the multi-stranded nucleic acids. Preferred examples of nucleic acids include double-stranded DNA, double-stranded RNA, DNA/RNA hybrids, and artificial double-stranded nucleic acids such as PNAs. However, even single-stranded nucleic acids can be determined by the detection method if they can be stained with the dye, such as when a plurality thereof are copresent.

The chromogenic leuco dye is a leuco dye that becomes colored when reacted with a color developer. Leuco dyes are colorless or pale-colored dyes that change in structure due to the reaction with a color developer or physical stimuli such as light, so that they exhibit changes in color. Known color developers include oxidizing agents and alcohols, but in the detection method a multi-stranded nucleic acid is used as the color developer.

The detection principle of the detection method is based on changes in color that occur as a result of the interaction between a chromogenic leuco dye and a multi-stranded nucleic acid when the leuco dye is added to the multi-stranded nucleic acid to bring the leuco dye into contact with the multi-stranded nucleic acid. The interaction here means that any physicochemical effect on the leuco dye is caused from the reversible binding to the multi-stranded nucleic acid.

The leuco dye is preferably a compound represented by General Formula (I):

(I)

wherein a leaving group of the leuco dye is dissociated by the interaction with the multi-stranded nucleic acid, and a color that can be detected under visible light is then formed by dissociation of the leaving group.

In General Formula (I) above, $R^1$, $R^2$ and $R^3$ each independently represent a substituted or unsubstituted aryl group. Examples of the aryl group include phenyl, naphthyl and anthracenyl groups and the like. These aryl groups may also be substituted with a functional group such as an amino group, hydroxyl group, alkoxy group, carbonyl group, carboxyl group, sulfonate group or alkyl group, and/or a halogen atom or other atoms.

L represents a leaving group, and specifically represents —$SO_3R^4$, —$NO_3$, —$NO_2$, —CN, —X, —$NHR^5$, —$N(COR^6)(COR^7)$, —$SR^8$, —$SSR^9$, —$OR^{10}$, —$NHSNH_2$, —OH or —H.

$R^4$ represents an alkali metal or a hydrogen atom. X represents a halogen atom such as F, Cl, Br or I. $R^5$, $R^6$, $R^7$, $R^8$, $R^9$ and $R^{10}$ each independently represent an alkyl group, aryl group, acyl group, alkenyl group or alkynyl group, and these substituents may also be substituted with another common functional group or atom, such as hetero functional groups such as amino groups, and halogen atoms.

The leuco dye is a dye that forms color due to an oxidation-reduction reaction or other reactions, and may be a reaction product of a nucleophile and a colored dye. For example, when a nucleophile is reacted with a colored triarylmethane dye, the dye can be converted to a leuco dye. Here, even when a single triarylmethane dye is used, leuco dyes with different structures can be obtained by varying the type of nucleophile used.

The dye is not particularly limited as long as it, forms color due to an oxidation-reduction reaction or other reactions, and exhibits a color that can be detected under visible light, as a result of the interaction with a multi-stranded nucleic acid. Examples thereof include triarylmethane dyes, xanthene dyes, quinoline dyes, phenothiazine dyes and phenoxazine dyes, and mixtures of these. Of these, triarylmethane dyes are preferred.

Compounds represented by General Formula (II):

(II)

are preferred as triarylmethane dyes. In the formula, L is defined as above, and $R^{11}$ and $R^{12}$ each independently represent a substituted or unsubstituted aryl group.

The substituted aryl group is an aryl group containing one or more substituents selected from a halogen atom, a hydroxyl group, an alkoxy group, an alkoxy group substituted with a halogen atom, an alkoxy group substituted with an aryl group, an aryloxy group, an alkyl group, an alkyl group substituted with a halogen atom, an alkyl group substituted with a hydroxyl group, an alkyl group substituted with an ester of a carboxyl group, an alkyl group substituted with a cyano group, a cycloalkyl group, an alkenyl group, an alkynyl group, an aryl group, a heterocyclic group, an amino group, an alkylamino group, an arylamino group, an amino group substituted with an alkylsulfonyl group, an amino group substituted with an acyl group, a mercapto group, an alkylthio group, an alkylthio group substituted with a halogen atom, an arylthio group, a carboxyl group or its ester or amide, a carbonyl (or oxo) group, a formyl group, an alkylcarbonyl group, an arylcarbonyl group, a thiocarbonyl (or thioxo) group, a cyano group, a nitro group, a sulfonate group, an alkylsulfonyl group, an alkylsulfonyl group substituted with a halogen atom, and an arylsulfonyl group.

$R^{13}$, $R^{14}$, $R^{15}$, $R^{16}$ and $R^{17}$ each independently represent, for example, a halogen atom or a carboxyl group, sulfo group, nitro group, cyano group, amino group, amino group, alkyl group, aryl group, alkenyl group, alkynyl group, hydroxyl group, alkoxy group, aryloxy group, alkylthio group, arylthio group, alkylamino group, arylamino group, acyl group, alkoxycarbonyl group, aryloxycarbonyl group, alkylsulfonyl group, arylsulfonyl group or the like.

It may be thought that the dye exhibits color via the mechanism shown in Reaction Formula (III) as a result of the interaction with a multi-stranded nucleic acid:

(III)

but the coloring mechanism is not particularly limited.

Specific examples of triarylmethane dyes include methyl green, malachite green, crystal violet, pararosaniline, gentian violet B, gentian violet R, night blue, victoria blue B, victoria blue R and other leuco derivatives. Of these, crystal violet, gentian violet, methyl green and malachite green are preferred, and crystal violet and gentian violet are more preferred.

In addition to the triarylmethane dyes, the following may be mentioned: the quinoline dye 4-(p-dimethylaminostyryl) quinoline, the phenothiazine dyes phenothiazine and benzoyl leucomethylene blue, the phenoxazine dye phenoxazine, and other leuco derivatives. However, the dye is not limited to these as long as it forms color by contact with a multi-stranded nucleic acid.

Examples of the nucleophile that reacts with a colored dye to convert it to a leuco dye include sodium sulfite and others containing sulfite ions, sodium hydrogen sulfite and others containing hydrogen sulfite ions, sodium nitrate and others containing nitrate ions, sodium nitrite and others containing nitrite ions, sodium cyanide and other containing cyanide ions, halide ions, nitrogen nucleophiles, sulfur nucleophiles, alkali metal alkoxides, alkali metal hydroxides, hydride nucleophiles and the like, but the nucleophile is not particularly limited as long as it allows the dye to be converted to the leuco form and then to be reconverted to the colored form by the interaction with a multi-stranded nucleic acid.

Examples of halide ions include fluoride ions, chloride ions, bromide ions, iodide ions and the like.

Examples of nitrogen nucleophiles include ammonia, methylamine, n-propylamine, dimethylamine, benzylamine, N-methylbenzylamine, aniline, n-heptylamine, 1-aminodecane, 1,3-diaminopropane and other amine nucleophiles; acetylamide and other amide nucleophiles; diacetylimide, diformylimide, phthalimide, metal salts of phthalimide and other imide nucleophiles; and benzenesulfonylamide, p-nitrobenzenesulfonylamide, o-nitrobenzenesulfonylamide, m-nitrobenzenesulfonylamide, p-toluenesulfonylamide and other sulfonylamide nucleophiles, and the like.

Examples of sulfur nucleophiles include thiols, disulfides, thiourea and the like.

Examples of alkali metal alkoxides include sodium methoxide, sodium ethoxide, potassium tert-butoxide and the like.

Examples of alkali metal hydroxides include sodium hydroxide, potassium hydroxide and the like.

Hydride nucleophiles are reagents capable of donating hydrogen as nucleophiles, and examples include sodium triacetoxyhydroborate, sodium borohydride, lithium tetrahydroborate, pyridine-borane complex, tetrahydrofuran-borane complex, 2-picoline-borane complex, dimethyl sulfide-borane complex, sodium cyanoborohydride, lithium triethylborohydride, lithium aluminum hydride, Red-Al (sodium bis(2-methoxyethoxy)aluminum hydride), L-Selectride (lithium tri(sec-butyl)borohydride), K-Selectride (potassium tri(sec-butyl)borohydride), DIBAL-H (diisobutylaluminum hydride) and the like.

Specifically, sodium sulfite, sodium hydrogen sulfite, n-propylamine, mercaptoethanol, sodium hydroxide and potassium hydroxide are preferred as nucleophiles, and sodium sulfite, mercaptoethanol and sodium hydroxide are more preferred.

With respect to the combination of the dye and the nucleophile, preferred are combinations of crystal violet and sodium sulfite, of gentian violet and sodium sulfite, of crystal violet and sodium hydroxide, of methyl green and 2-mercaptoethanol, of methyl green and sodium sulfite, and of malachite green and sodium sulfite. Of these, combinations of crystal violet and sodium sulfite, of gentian violet and sodium sulfite, and of methyl green and sodium sulfite are more preferred.

In the step of bringing a chromogenic leuco dye into contact with a multi-stranded nucleic acid, the two may be brought into contact in any way as long as the chromogenic leuco dye contacts the multi-stranded nucleic acid so that a reaction occurs between the two.

With respect to the detection under visible light of a color formed by interaction between the leuco dye and the multi-stranded nucleic acid, the color is detected under visible light such as lighting in an ordinary laboratory, without exposure to light other than visible light such as ultraviolet light. In the case of visible light, detection can be simplified because no special equipment is required as in the case of ultraviolet irradiation.

The simplest method for detecting a multi-stranded nucleic acid is by visually observing changes in color resulting from contact between the leuco dye and the multi-stranded nucleic acid. Visually observing, as used herein, means visually observing changes in the color of the leuco dye when it is bound to the multi-stranded nucleic acid, or changes in the color of the leuco dye when it is not bound to the multi-stranded nucleic acid. The presence or absence of a multi-stranded nucleic acid can be confirmed based on changes in color under visible light.

Specific examples of changes in color include changes in the type of color under visible light (visible light wavelength), and changes in the concentration of color (reflectance), but are not limited to these as long as the changes can be detected under visible light. Exemplary changes in the type of color include, for example, the changes from reddish-violet to aqua and the changes from yellow to reddish-violet.

The nucleic acid can also be detected by measuring the absorbance of a sample solution in the visible light range. Visible light, as used herein, indicates light at wavelengths of 380 nm to 800 nm in particular. The measurement wavelength can be set appropriately according to the dye used. It is also possible to assay the nucleic acid concentration in a sample by absorbance measurement. In addition, when an insoluble precipitate is formed of the dye and nucleic acid, the precipitate can be detected with a filter or membrane, or by centrifugation. A dye of a different color may also be mixed in to make it easier to determine the presence or absence of the nucleic acid.

A multi-stranded nucleic acid contained in a test sample can be detected by the detection method, and the test sample is not particularly limited as long as it contains a multi-stranded nucleic acid. In addition to reaction liquids resulting from nucleic acid amplification methods, liquid extracts from microorganisms, animal cells and plant cells can also be used; moreover, liquid extracts from foodstuffs can suitably be used.

The nucleic acid amplification method can be any method that amplifies a nucleic acid sequence, such as typically PCR. Examples of methods other than PCR include, but are not limited to, known methods such as LCR (ligase chain reaction), SDA (strand displacement amplification), RCA (rolling circle amplification), CPT (cycling probe technology), Q-beta replicase amplification technology, ICAN (isothermal and chimeric primer-initiated amplification of nucleic acids), LAMP (loop-mediated isothermal amplification of DNA), NASBA (nucleic acid sequence-based amplification method) and TMA (transcription mediated amplification method). Q-beta replicase amplification technology, RCA, NASBA, SDA, TMA, LAMP, ICAN and the like involve an amplification reaction at a fixed temperature, while other methods such as PCR and LCR involve an amplification reaction via temperature cycling. In addition, when RNA is reverse transcribed into DNA by a reverse transcriptase or the like, the RNA can then be detected indirectly by a nucleic acid amplification method as mentioned above using this DNA as a template.

In the case of detecting a multi-stranded nucleic acid that is an amplified product of a nucleic acid amplification method, the leuco dye is preferably added to the reaction liquid after the nucleic acid amplification reaction, or alternatively the leuco dye may also be added to the reaction liquid in advance before the nucleic acid amplification reaction.

The leuco dye may be added alone to a test sample containing a multi-stranded nucleic acid, or it may be added in the form of a mixture with a stabilizer.

The stabilizer is a compound that prevents coloring of the leuco dye, and may, for example, be a reducing agent, an amine or thiol compound or the like although it is not limited to these as long as it prevents coloring. The stabilizer may be added alone, or a combination of more than one may be added.

Moreover, the leuco dye may be added directly to a test sample containing a multi-stranded nucleic acid, or alternatively a colored dye may be treated with a nucleophile or the like so as to be converted to a leuco dye before addition. Alternatively, a mixture of a nucleophile and a colored dye may be added. For example, crystal violet may be mixed with sodium sulfate to be converted to a leuco dye, and this mixture can then be used for visual detection of a multi-stranded nucleic acid. It is particularly effective to use a liquid mixture of a nucleophile and a colored dye when the leuco dye is unstable and difficult to isolate.

The amount of leuco dye added to the test sample containing the nucleic acid is not particularly limited as long as the coloration can be observed. The final concentration is typically 10% or less, preferably 1% or less, and more preferably 0.1% or less.

The colored test sample liquid after nucleic acid detection can be used as is for other molecular biological operations. Such molecular biological operations include restriction enzyme treatment, sequencing reactions, and PCR and other enzyme reactions, as well as identification operations based on electrophoresis, and the like.

2. Nucleic Acid Detection Device and Kit

The present invention also relates to a device or kit for detecting a multi-stranded nucleic acid, comprising: (d) a carrier carrying a leuco dye, (e) a pathway for a test sample to pass through the carrier (d), and (f) a part for detecting under visible light the color change exhibited by interaction between the test sample and the leuco dye to determine the presence of a multi-stranded nucleic acid.

The material of the carrier (d) carrying a leuco dye is not particularly limited as long as it can carry the dye and allow passage of a test sample containing a nucleic acid. Preferred specific examples include nonwoven fabrics, filter paper, fiberglass filter paper, fiberglass cloth, glass filters, nitrocellulose filters, and porous materials of polyethylene, polypropylene or the like. The leuco dye may be fixed on the carrier (d) by a known method such as physical adsorption, chemical binding or the like. Physical adsorption may be accomplished for example by drying adsorption in which the carrier is impregnated with a certain amount of a dye solution and then dried.

The amount of leuco dye carried by the carrier (d) is not particularly limited as long as the color change can be detected under visible light. The final concentration of the dye after mixing with a test sample containing a nucleic acid is preferably 10% or less, more preferably 1% or less, and still more preferably 0.1% or less.

When a test sample passes through the carrier (d) carrying a leuco dye, and the test sample contains a multi-stranded nucleic acid, the multi-stranded nucleic acid interacts with the leuco dye so that a leaving group is dissociated from the leuco dye, thereby causing changes in color. The interaction herein may be, but is not limited to, covalent binding such as peptide binding or disulfide binding, or non-covalent binding such as ion binding, coordinate binding, Van der Waals binding or $\pi$-$\pi$ interaction.

The interaction between the multi-stranded nucleic acid and the leuco dye on the carrier (d) may be affected by the affinity between the multi-stranded nucleic acid and the carrier, and by the hygroscopicity of the carrier. Therefore, the carrier may be impregnated or surface coated with a hydrophilic polymer or surfactant in order to control the non-specific adsorption of the multi-stranded nucleic acid or the hygroscopicity.

The pathway (e) for a test sample to pass through the carrier (d) is a pathway through which a test sample applied to the device or kit of the present invention moves. The pathway is not particularly limited as long as it induces movement of the test sample. The pathway may be provided with a groove, although this is not a requirement. The pathway (e) is connected to the carrier (d) and the determination part (f), so that the test sample can move along the pathway (e) to the carrier (d) and the determination part (f). The material of the pathway (e) is not particularly limited as long as it allows passage of a test sample containing a multi-stranded nucleic acid.

The determination part (f) for detecting under visible light the color change exhibited by interaction between the test sample and the dye to determine the presence of a multi-stranded nucleic acid is a part that the test sample passing through the carrier (d) arrives at via the pathway (e).

The presence or absence of a multi-stranded nucleic acid can be determined by detecting changes in color at the determination part (f) under visible light, without the need for specialized equipment such as a UV irradiation device, fluorescence detection device or the like.

The material of the determination part (f) is not particularly limited as long as it allows passage or absorption of a test sample containing a multi-stranded nucleic acid. Preferred specific examples include nonwoven fabrics, filter paper, fiberglass filter paper, fiberglass cloth, glass filters, nitrocellulose filters, and porous materials of polyethylene, polypropylene or the like. These materials have a suitable rate of moisture absorption and are also advantageous in terms of visual observation of color when color is developed by a multi-stranded nucleic acid.

It is also possible to estimate the concentration of a multi-stranded nucleic acid in a test sample by preparing a correlation table showing the degree of coloration depending on the amount of the multi-stranded nucleic acid. By preparing a calibration curve using nucleic acid standards of known concentrations, it is also possible to assay the amount of a multi-stranded nucleic acid in a sample with widely-used analysis equipment such as a spectrophotometer, color difference meter or reflection meter.

The method for applying a test sample to the multi-stranded nucleic acid detection device or kit is not particularly limited, and the test sample may be applied for example by dripping, immersion, suction or centrifugation. After the test sample is added, it may also be developed with a separate solvent. In the case of developing with a solvent, the solvent used is not particularly limited unless it affects the color of the dye, and examples include water and buffers. The multi-stranded nucleic acid detection device or kit of the present invention may also be provided with a separate sample addition part. The test sample may also be applied directly to the carrier (d) carrying a leuco dye.

The carrier (d) may carry the leuco dye alone, or may carry the leuco dye together with a stabilizer. The stabilizer may be an amine, thiol, reducing agent or the like, although it is not limited to these as long as it suppresses self-coloring of the leuco dye. Moreover, instead of the leuco dye carried directly by the carrier, a colored dye and a compound that reacts with the dye to change it into the leuco form may be mixed and included together on the carrier. Examples of the compound that reacts with a colored dye to change it into the leuco form include, but are not limited to, sulfite ions, hydrogen sulfite ions, nitrate ions, nitrite ions, cyanide ions, halide ions, nitrogen nucleophiles, sulfur nucleophiles, alkali metal alkoxides, alkali metal hydroxides, hydride nucleophiles and other nucleophiles. A carrier carrying a stabilizer or a different kind of dye may also be disposed downstream and/or upstream from the carrier (d). In this case, the carriers (d) and (e) may or may not be in contact with each other. Another carrier(s) may also be disposed between the two carriers and/or before or after the two. Moreover, a region where the test sample is applied, a region for determining color or another region may, if necessary, be provided separately.

The member that is a substrate for the carrier to be disposed is not particularly limited as long as it can support the carrier, and examples of its material are plastic, paper, glass and other materials. The surface thereof may also be adhesive.

With the multi-stranded nucleic acid detection device or kit, a multi-stranded nucleic acid can be detected easily and rapidly through color formation due to a reaction between the multi-stranded nucleic acid and the leuco dye.

Specific examples of the multi-stranded nucleic acid detection device and kit according to this embodiment are shown in FIGS. 1 to 4.

Figure 1:
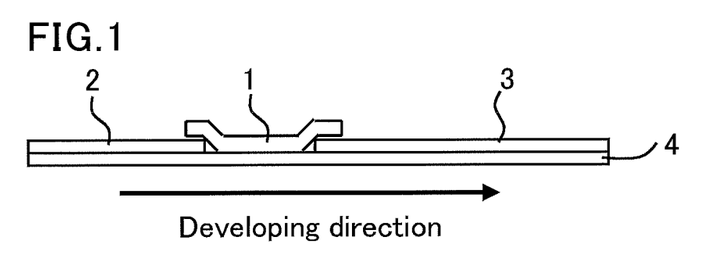
FIG. 1 is a schematic view of an exemplary chromatography-type device for nucleic acid detection according to the present invention.

FIG. 1 shows a chromatography-type device for multi-stranded nucleic acid detection. This detection device includes a carrier 1 carrying a leuco dye, a sample addition part 2 and a determination part 3, bonded by means of a pressure-sensitive adhesive or the like onto a member 4 as a substrate.

Figure 2:
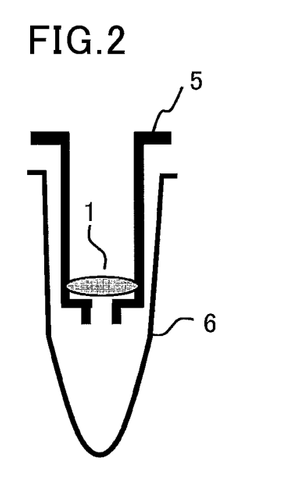
FIG. 2 is a schematic view of an exemplary filter-type device for nucleic acid detection according to the present invention.

FIG. 2 shows a filter-type device for multi-stranded nucleic acid detection. In the device of FIG. 2, a test sample is applied inside a supporting body 5 and then, while being in contact with a leuco dye carried by a carrier 1, is received in a test sample container 6. With this configuration, the presence or absence or the amount of a multi-stranded nucleic acid contained in the test sample can be determined based on the color of the test sample solution contained in the test sample container 6. The presence or absence or the amount of a multi-stranded nucleic acid can be determined very rapidly and easily if the test sample is allowed to pass through the filter-type carrier by centrifugation, increased pressure or the like.

Figure 3:
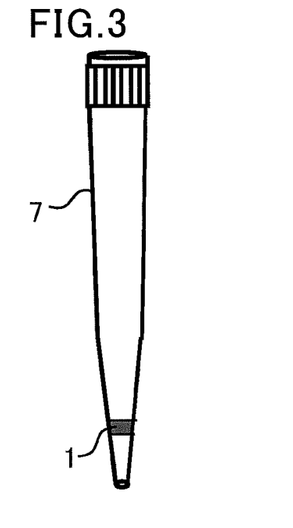
FIG. 3 is a schematic view of an exemplary suction-type device for nucleic acid detection according to the present invention.

FIG. 3 shows a suction-type device for multi-stranded nucleic acid detection. The detection device of FIG. 3 is composed of a carrier 1 carrying a leuco dye and a supporting body 7 that forms a suction device. In FIG. 3, a micropipette tip is used as an example of the supporting body that forms a suction device, and in this case a micropipettor is mounted on the upper opening of the tip and then used to suction a test sample through a suction opening. This embodiment is not limited in application to micropipette tips, and can also be applied suitably to pipettes such as Pasteur pipettes and Komagome pipettes, capillary devices, syringes and the like. With this configuration, the presence or absence of a multi-stranded nucleic acid can be visually detected very rapidly and easily based on the color of the dye by using each of such suction devices including a carrier to suction a test sample.

Figure 4:
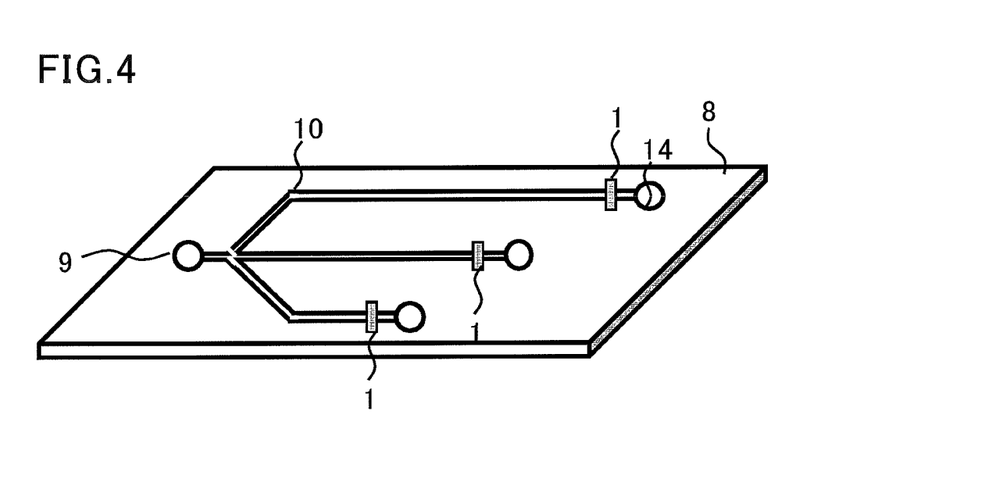
FIG. 4 is a schematic view of an exemplary channel-type device for nucleic acid detection according to the present invention.

FIG. 4 shows a channel-type device for multi-stranded nucleic acid detection. The channel-type device shown in FIG. 4 characteristically includes a carrier 1 carrying a leuco dye, disposed on a chip 8 having a channel cut therein. This chip may include a mechanism for nucleic acid purification, nucleic acid amplification or the like. In the detection device according to this embodiment, a test sample applied to a sample addition part 9 moves along a channel 10 and passes through the carrier 1 to arrive finally at a determination part 14. The presence or absence or the amount of a multi-stranded nucleic acid can be determined visually by observing the color exhibited at the determination part 14 under visible light. The shape of channel 10 is not particularly limited, and may be straight or curved for example. As shown in FIG. 4, if multiple combinations of the channel and carrier are provided on the chip 8, the passage time of the test sample along the channel 10 until reaching the determination part 14 can be varied by varying the length of channel. When the chip 8 includes a mechanism for nucleic acid amplification, the amount of nucleic acid amplified can be varied by varying the passage time of the test sample, and therefore nucleic acid amplification and detection of the resulting product can be performed in stages.

3. Nucleic Acid Detection Device and Kit

The present invention also relates to a device or kit for detecting a multi-stranded nucleic acid, comprising: (g) a carrier carrying a leuco dye and provided with an opening that is opened by external force to release the leuco dye; h) a pathway for conducting the released leuco dye to a determination part; and (i) the determination part for retaining an introduced test sample and detecting under visible light changes in color resulting from a reaction between the retained test sample and the leuco dye introduced from the carrier (g) via the pathway (h) to determine the presence of a multi-stranded nucleic acid.

The material of the carrier (g) carrying a leuco dye and provided with an opening that is opened by external force to release the leuco dye is not particularly limited as long as it can carry the leuco dye stably for a certain period of time. The carrier (g) is loaded with the leuco dye, and the opening for releasing the leuco dye is normally closed so that the leuco dye is only released when the opening of the carrier (g) is opened by external force. The external force herein is not particularly limited as long as it can open the carrier, and examples include pushing down with a finger or pushing down by mechanical means. The mode of opening by external force is not particularly limited as long as the leuco dye can be released, and examples include breaking of a membrane carrying a leuco dye. The device or kit according to this embodiment may also be provided with a needle-shaped structure to facilitate opening of the carrier (g).

The pathway (h) for conducting the released leuco dye to the determination part is a pathway through which the leuco dye released from the carrier (g) passes. The shape and material of the pathway (h) are not particular limited as long as they allow passage of the leuco dye. For example, when the released leuco dye drops by gravitational force to arrive at the determination part (i), the pathway (h) can be any that does not impede the dropping of the leuco dye.

The determination part (i) for retaining an introduced test sample and observing a substance produced by a reaction between the retained test sample and the leuco dye introduced from the carrier (g) via the pathway (h) under visible light to visually determine the presence of a multi-stranded nucleic acid is as explained in the context of the device or kit for detecting a multi-stranded nucleic acid according to the first embodiment of the present invention.

Figure 5:
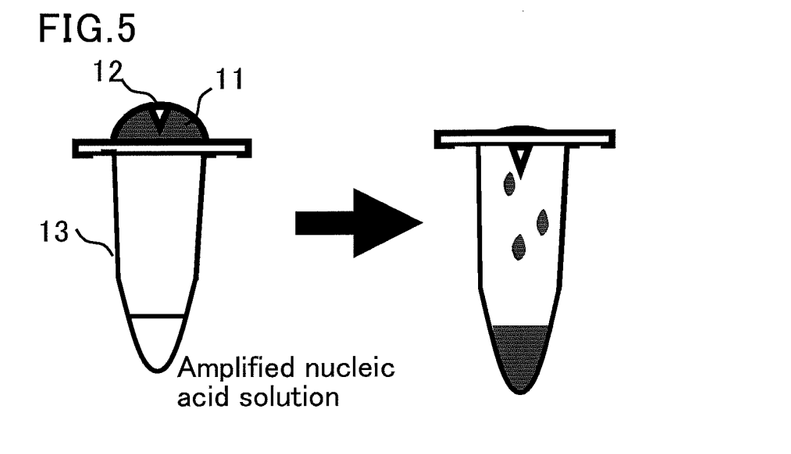
FIG. 5 is a schematic view of an exemplary tube-type device for nucleic acid detection according to the present invention.

A specific example of the multi-stranded nucleic acid detection device according to this embodiment is shown in FIG. 5.

FIG. 5 shows a tube-type device for multi-stranded nucleic acid detection. This tube-type device also encompasses those including a mechanism that allows a dye to be added to a nucleic acid solution by external physical action. In FIG. 5 for example, a leuco dye 11 is carried by a membrane at the cap part of a tube 13, and in this case breaking the membrane by external physical action (such as pushing with a finger) using a needle-shaped structure 12 incorporated in the cap causes the leuco dye 11 to drop into the bottom of the tube, thereby staining a multi-stranded nucleic acid contained in a test sample at the bottom of the tube.

In the present invention, the multi-stranded nucleic acid detection kit refers to a form provided with various reagents, tools and the like in addition to a detection unit including a solution of a leuco dye for specifically coloring a multi-stranded nucleic acid. Those including the devices described above added thereto are also considered the kits. The various reagents include primers and DNA polymerases for amplifying target nucleic acids, and buffers and restriction enzymes used in nucleic acid amplification reactions, and the like.

The colored test sample containing a multi-stranded nucleic acid, obtained using such a device can be used as is for other molecular biological operations. Examples of such molecular biological operations include restriction enzyme treatment, sequencing reactions, and PCR and other enzyme reactions, as well as identification operations based on electrophoresis, and the like.

The multi-stranded nucleic acid detection device of the present invention may also be incorporated into an apparatus for automatically treating test samples and analyzing base sequences and the like. For example, when the nucleic acid detection device of the present invention is incorporated into an apparatus for nucleic acid purification or amplification, it is possible to determine the presence or absence of nucleic acid; or when it is incorporated into an automatic DNA analysis apparatus, it is possible to reliably select and analyze only a sample that has been amplified and labeled by PCR.

EXAMPLES

The present invention is explained in detail below referring to examples. However, these examples do not restrict the technical scope of the present invention.

Example 1

Detection of PCR Product Using Leuco Dye (1)

(i) Synthesis of Leuco Dye (1)

500 mg of crystal violet was dissolved in water, after which 200 mg of n-propylamine was added and stirred for 30 minutes. The resulting precipitate was dried to obtain 450 mg of a leuco dye (1) (1,1-tris(4-N,N-dimethylaminophenyl)-N-aminopropane).

(ii) Preparation of PCR Product

The following Primer F: 5'-GGAAACAGCTATGAC-CATGA-3' and Primer R: 5'-CTATGCGGCATCAGAG-CAG-3' were designed so as to allow a sequence of roughly 330 base pairs to be amplified by PCR amplification using pUC19 (Takara Bio Inc.) as a template. 15 pmol each of Primer F and Primer R and 10 ng of pUC19 were placed in a 0.2 ml PCR tube, and a 100 µl PCR reaction liquid was prepared in accordance with the manual of an ExTaq PCR Kit (Takara Bio Inc.). The tube was then set in a thermal cycler (GeneAmp PCR System (Applied Biosystems Inc.)), heat treated for 5 minutes at 95° C., and then subjected to 35 cycles of 30 seconds at 95° C., 30 seconds at 55° C. and 30 seconds at 72° C. to amplify the target sequence of roughly 330 bp as a positive control. As a negative control, a similar reaction was also performed with no ExTaq DNA polymerase added.

(iii) Detection of PCR Product

2 µg of the leuco dye (1) synthesized above was added to 50 µl of the positive control and of the negative control, and then the color change was observed and the absorbance (A590 nm) was measured. The results are shown in Table 1.

Comparative Example 1

A PCR product was detected by the same methods as in Example 1, except that gentian violet was used instead of the leuco dye. The results are shown in Table 1.

Example 2

Detection of LAMP Product Using Leuco Dye (1)

(i) Preparation of LAMP Product

A nucleic acid amplification reaction liquid was prepared by the LAMP method using a "Loopamp (R) Salmonella Detection Kit" (EIKEN CHEMICAL CO., LTD.). 10 µl of Control DNA Sal and 40 µl of a master mix (separately prepared by mixing Reaction Mix. Sal and Bst DNA polymerase at 20:1 by volume) were mixed, reacted for 1 hour at 65° C. and then reacted for 20 minutes at 80° C. to prepare a reaction liquid containing amplified nucleic acid (positive control). Separately, 10 µl of Control DNA Sal and 40 µl of Reaction Mix. Sal were mixed, reacted for 1 hour at 65° C. and then reacted for 20 minutes at 80° C. to prepare a reaction liquid without amplified nucleic acid (negative control).

(ii) Detection of LAMP Product

The procedure of Example 1 was followed except that the LAMP products were used as the test samples. The results are shown in Table 1.

TABLE 1

|  | Example 1 PCR | | Comparative Example 1 PCR | | Example 2 LAMP method | |
| --- | --- | --- | --- | --- | --- | --- |
| Nucleic acid amplification | − | + | − | + | − | + |
| Absorbance (590 nm) | 0.013 | 0.456 | 0.510 | 0.537 | 0.024 | 0.421 |
| Color | Colorless | Blue-violet | Blue-violet | Blue-violet | Colorless | Blue-violet |
| Visual detection | Possible | | Not Possible | | Possible | |

In Example 1, the color turned blue-violet immediately after addition of the lueco dye in the case of the positive control with nucleic acid amplification by PCR. In the case of the negative control with no nucleic acid amplification by PCR, on the other hand, there was no coloring after addition of the leuco dye; therefore, the presence or absence of nucleic acid amplification could be easily determined visually. The time required for detection with the dye was 1 minute or less.

In Comparative Example 1, a blue-violet color appeared regardless of whether there was nucleic acid amplification, and it was difficult to determine the presence or absence of the nucleic acid.

In Example 2, the color turned blue-violet immediately after addition of the leuco dye in the case of the positive control with nucleic acid amplification by the LAMP method. In the case of the negative control with no nucleic acid amplification by the LAMP method, on the other hand, there was no coloring after addition of the leuco dye; therefore, the presence or absence of nucleic acid amplification could be easily determined visually. The time required for detection with the dye was 1 minute or less.

Example 3

Detection of Multi-Stranded Nucleic Acid Using Methyl Green

100 µl of a 0.2% methyl green aqueous solution and 50 µl of 2-mercaptoethanol were mixed, and reacted for 10 minutes at room temperature. PCR products and LAMP products were then prepared by the same methods as in Examples 1 and 2. 2 µl of the liquid mixture prepared was added to 50 µl each of the negative controls and the positive controls of the amplified nucleic acid products, and then the color change was observed. The results are shown in Table 2.

TABLE 2

|  | Example 3 | | | |
| --- | --- | --- | --- | --- |
|  | PCR | | LAMP method | |
| Nucleic acid amplification | − | + | − | + |
| Absorbance (630 nm) | 0.013 | 0.256 | 0.021 | 0.338 |
| Visual detection | Possible | | Possible | |

In the case of the positive controls with nucleic acid amplification by PCR and LAMP methods, the color turned blue-green immediately after addition of the liquid mixture of methyl green and 2-mercaptoethanol. In the case of the negative controls with no nucleic acid amplification, on the other hand, there was no coloring after addition of the liquid mixture; therefore, the presence or absence of nucleic acid amplification could be easily determined visually. The time required for detection with the dye was 1 minute or less.

Example 4

Detection of Multi-Stranded Nucleic Acid Using Gentian Violet B

A 0.2% gentian violet b solution in 50% ethanol was mixed with an equal volume of a 6% sodium sulfite aqueous solution. PCR reaction liquids and LAMP reaction liquids were prepared by the same methods as in Examples 1 and 2. 1 µl of the liquid mixture prepared was added to 50 µl each of the negative controls and the positive controls of the amplified nucleic acid products, and then the color change was observed. The absorbance was then measured at 590 nm. The results are shown in Table 3.

TABLE 3

|  | Example 4 | | | |
| --- | --- | --- | --- | --- |
|  | PCR | | LAMP method | |
| Nucleic acid amplification | − | + | − | + |
| Absorbance (590 nm) | 0.013 | 0.389 | 0.015 | 0.442 |

TABLE 3-continued

|  | Example 4 | | | |
| --- | --- | --- | --- | --- |
|  | PCR | | LAMP method | |
| Color | Colorless | Blue-violet | Colorless | Blue-violet |
| Visual detection | Possible | | Possible | |

In the case of the positive controls with nucleic acid amplification by PCR and LAMP methods, the color turned blue-violet immediately after addition of the liquid mixture. In the case of the negative controls with no nucleic acid amplification, on the other hand, there was no coloring after addition of the liquid mixture; therefore, the presence or absence of nucleic acid amplification could be easily determined visually. The time required for detection with the dye was 1 minute or less.

Example 5

Preparation of Suction-Type Device

A 0.2% solution of the leuco dye (1) synthesized in Example 1 was prepared, and a porous polyethylene sheet punched in a circular shape (pore diameter 50 µm, thickness 1.5 mm, diameter 1.5 mm) was impregnated with 1 µl of this solution. The impregnated product was dried at room temperature to obtain a carrier carrying the dye. This carrier was packed in the tip of a 200 µl pipette tip to prepare a suction-type device as shown in FIG. 3.

Example 6

Detection of Multi-Stranded Nucleic Acid with Suction-Type Device

PCR products and LAMP products were prepared by the same methods as in Examples 1 and 2 to obtain positive and negative controls. The suction-type device prepared in Example 5 was mounted on a micropipette, 100 µl of each test sample was suctioned, and the color of the test sample solution inside the pipette tip was observed. The results are shown in Table 4.

Example 7

Preparation of Suction-Type Device

Equal volumes of 0.2% gentian violet and 6% sodium sulfite were mixed, and a porous polyethylene sheet punched in a circular shape (pore diameter 50 µm, thickness 1.5 mm, diameter 1.5 mm) was impregnated with 1 µl of this liquid mixture. The impregnated product was dried at room temperature to obtain a carrier carrying the dye. This carrier was packed in the tip of a 200 µl pipette tip to prepare a suction-type device as shown in FIG. 3.

Example 8

Detection of Multi-Stranded Nucleic Acid with Suction-Type Device

PCR products and LAMP products were prepared by the same methods as in Examples 1 and 2 to obtain positive and negative controls. The suction-type device prepared in Example 7 was mounted on a micropipette, 100 µl of each test sample was suctioned, and the color of the test sample solution inside the pipette tip was observed. The results are shown in Table 4.

TABLE 4

| | Example 6 | | | | Example 8 | | | |
|---|---|---|---|---|---|---|---|---|
| | PCR | | LAMP method | | PCR | | LAMP method | |
| Nucleic acid amplification | − | + | − | + | − | + | − | + |
| Color | Colorless | Blue-violet | Colorless | Blue-violet | Colorless | Blue-violet | Colorless | Blue-violet |
| Visual detection | | Possible | | Possible | | Possible | | Possible |

In Example 6, the test sample solution inside the tip exhibited a blue-violet color when there was nucleic acid amplification by PCR and LAMP methods, whereas it was colorless and transparent when no amplified nucleic acid was present. The time required for detecting the amplified nucleic acid by the suction-type device was only a few seconds; therefore, rapid and simple visual determination was possible.

In Example 8 as well, the test sample solution inside the tip exhibited a blue-violet color when there was nucleic acid amplification by PCR and LAMP methods, whereas it was colorless and transparent when no amplified nucleic acid was present. The time required for detecting the amplified nucleic acid by the suction-type device was only a few seconds; therefore, rapid and simple visual determination was possible.

Example 9

Investigation of Treatment Using Colored Sample

Coloring of PCR products was performed by the same methods as in Examples 1 and 3, and the colored samples were subjected to electrophoresis, PCR, restriction enzyme treatment and a sequencing reaction. As a result, the coloring of nucleic acid according to the present invention had no effect on the subsequent treatments, which were accomplished well in all cases.

Reference Signs List

1. Carrier carrying leuco dye that forms color by contact with multi-stranded nucleic acid
2. Sample addition part (fiberglass filter paper)
3. Determination part (filter paper)
4. Substrate
5. Supporting body supporting carrier
6. Test sample container
7. Pipette tip
8. Chip with channel
9. Sample addition part
10. Channel
11. Dye
12. Needle-shaped structure
13. Tube
14. Determination part

The invention claimed is:

1. A method for detecting a multi-stranded nucleic acid, comprising a step of bringing a chromogenic leuco dye into contact with a multi-stranded nucleic acid, wherein a color formed by interaction between the leuco dye and the multi-stranded nucleic acid is detected under visible light, and wherein the leuco dye is a compound represented by General Formula (I):

wherein $R^1$, $R^2$ and $R^3$ each independently represent a substituted or unsubstituted aryl group, and L represents —$SO_3R^4$, —$NO_3$, —$NO_2$, —CN, —X, —$NHR^5$, —$N(COR^6)(COR^7)$, —$SR^8$, —$SSR^9$, —$OR^{10}$, —$NHSNH_2$, —OH or —H, with $R^4$ representing an alkali metal or a hydrogen atom; X representing a halogen atom; and $R^5$, $R^6$, $R^7$, $R^8$, $R^9$ and $R^{10}$ each independently representing an alkyl group, aryl group, acyl group, alkenyl group or alkynyl group, and wherein a leaving group of the leuco dye is dissociated by interaction between the leuco dye and the multi-stranded nucleic acid, and a color that can be detected under visible light is then formed by dissociation of the leaving group.

2. The detection method according to claim 1, wherein the compound represented by General Formula (I) is a compound represented by General Formula (II):

wherein L is defined as in claim 1; $R^{11}$ and $R^{12}$ each independently represent a substituted or unsubstituted aryl group; and $R^{13}$, $R^{14}$, $R^{15}$, $R^{16}$ and $R^{17}$ each independently represent a halogen atom or a carboxyl group, sulfo group, nitro group, cyano group, amido group, amino group, alkyl group, aryl group, alkenyl group, alkynyl group, hydroxy group, alkoxy group, aryloxy group, alkylthio group, arylthio group, alkylamino group, arylamino group, acyl group, alkoxycarbonyl group, aryloxycarbonyl group, alkylsulfonyl group or arylsulfonyl group.

3. The detection method according to claim 2, wherein the leuco dye is a reaction product of a triarylmethane dye and a nucleophile.

4. The detection method according to claim 3, wherein the triarylmethane dye is one or more dyes selected from the group consisting of gentian violet, crystal violet, methyl green, malachite green, victoria blue and pararosaniline, and derivatives thereof.

5. The detection method according to claim 3, wherein the nucleophile is one or more nucleophiles selected from the group consisting of sulfite ions, hydrogen sulfite ions, nitrate ions, nitrite ions, cyanide ions, halide ions, nitrogen nucleophiles, sulfur nucleophiles, alkali metal alkoxides, alkali metal hydroxides and hydride nucleophiles.

6. The detection method according to claim 1, wherein the leuco dye is a reaction product of a triarylmethane dye and a nucleophile.

7. The detection method according to claim 6, wherein the triarylmethane dye is one or more dyes selected from the group consisting of gentian violet, crystal violet, methyl green, malachite green, victoria blue and pararosaniline, and derivatives thereof.

8. The detection method according to claim 7, wherein the nucleophile is one or more nucleophiles selected from the group consisting of sulfite ions, hydrogen sulfite ions, nitrate ions, nitrite ions, cyanide ions, halide ions, nitrogen nucleophiles, sulfur nucleophiles, alkali metal alkoxides, alkali metal hydroxides and hydride nucleophiles.

9. The detection method according to claim 6, wherein the nucleophile is one or more nucleophiles selected from the group consisting of sulfite ions, hydrogen sulfite ions, nitrate ions, nitrite ions, cyanide ions, halide ions, nitrogen nucleophiles, sulfur nucleophiles, alkali metal alkoxides, alkali metal hydroxides and hydride nucleophiles.

10. A device or kit for detecting a multi-stranded nucleic acid, comprising:
(a) cal a carrier carrying a leuco dye, wherein the leuco dye is a compound represented by General Formula (I):

wherein $R^1$, $R^2$ and $R^3$ each independently represent a substituted or unsubstituted aryl group, and L represents —$SO_3R^4$, —$NO_3$, —$NO_2$, —CN, —X, —$NHR^5$, —$N(COR^6)(COR^7)$, —$SR^8$, —$SSR^9$, —$OR^{10}$, —$NHSNH_2$, —OH or —H, with $R^4$ representing an alkali metal or a hydrogen atom; X representing a halogen atom; and $R^5$, $R^6$, $R^7$, $R^8$, $R^9$ and $R^{10}$ each independently representing an alkyl group, aryl group, acyl group, alkenyl group or alkenyl group, and wherein a leaving group of the leuco dye is dissociated by interaction between the leuco dye and the multi-stranded nucleic acid, and a color that can be detected under visible light is then formed by dissociation of the leaving group;

(b) a pathway for a test sample to pass through the carrier (a); and (c) a part for detecting under visible light a color formed by interaction between the test sample and the leuco dye to determine the presence of a multi-stranded nucleic acid.

11. The device or kit according to claim 10, wherein the carrier (a) carries a liquid mixture of a triarylmethane dye and a nucleophile.

12. The device or kit according to claim 11, wherein the triarylmethane dye is one or more dyes selected from the group consisting of gentian violet, crystal violet, methyl green, malachite green, victoria blue and pararosaniline, and derivatives thereof.

13. The device or kit according to claim 12, wherein the nucleophile is one or more nucleophiles selected from the group consisting of sulfite ions, hydrogen sulfite ions, nitrate ions, nitrite ions, cyanide ions, halide ions, nitrogen nucleophiles, sulfur nucleophiles, alkali metal alkoxides, alkali metal hydroxides and hydride nucleophiles.

14. The device or kit according to claim 11, wherein the nucleophile is one or more nucleophiles selected from the group consisting of sulfite ions, hydrogen sulfite ions, nitrate ions, nitrite ions, cyanide ions, halide ions, nitrogen nucleophiles, sulfur nucleophiles, alkali metal alkoxides, alkali metal hydroxides and hydride nucleophiles.

15. The device or kit according to claim 10, wherein the compound represented by General Formula (I) is a compound represented by General Formula (II):

(II)

wherein L is defined as in claim 7; $R^{11}$ and $R^{12}$ each independently represent a substituted or unsubstituted aryl group; and $R^{13}$, $R^{14}$, $R^{15}$, $R^{16}$ and $R^{17}$ each independently represent a halogen atom or a carboxyl group, sulfo group, nitro group, cyano group, amido group, amino group, alkyl group, aryl group, alkenyl group, alkynyl group, hydroxy group, alkoxy group, aryloxy group, alkylthio group, arylthio group, alkylamino group, arylamino group, acyl group, alkoxycarbonyl group, aryloxycarbonyl group, alkylsulfonyl group or arylsulfonyl group.

16. The device or kit according to claim 15, wherein the carrier (a) carries a liquid mixture of a triarylmethane dye and a nucleophile.

17. The device or kit according to claim 16, wherein the triarylmethane dye is one or more dyes selected from the group consisting of gentian violet, crystal violet, methyl green, malachite green, victoria blue and pararosaniline, and derivatives thereof.

18. The device or kit according to claim 17, wherein the nucleophile is one or more nucleophiles selected from the group consisting of sulfite ions, hydrogen sulfite ions, nitrate ions, nitrite ions, cyanide ions, halide ions, nitrogen nucleophiles, sulfur nucleophiles, alkali metal alkoxides, alkali metal hydroxides and hydride nucleophiles.

19. The device or kit according to claim 16, wherein the nucleophile is one or more nucleophiles selected from the group consisting of sulfite ions, hydrogen sulfite ions, nitrate ions, nitrite ions, cyanide ions, halide ions, nitrogen nucleophiles, sulfur nucleophiles, alkali metal alkoxides, alkali metal hydroxides and hydride nucleophiles.

* * * * *